United States Patent [19]

Propp

[11] Patent Number: 5,282,794
[45] Date of Patent: Feb. 1, 1994

[54] GUARDED NEEDLE AND RETAINING MEANS

[75] Inventor: Donald J. Propp, Dewitt, Mich.

[73] Assignee: Tri-State Hospital Supply Corporation, Howell, Mich.

[21] Appl. No.: 933,762

[22] Filed: Aug. 24, 1992

[51] Int. Cl.$^5$ .............................................. A61M 25/00
[52] U.S. Cl. ..................................... 604/283; 604/411; 604/905; 604/244
[58] Field of Search ............... 604/192, 263, 283, 244, 604/403, 411, 416, 905, 86-88, 201, 206

[56] References Cited

U.S. PATENT DOCUMENTS

| | | | |
|---|---|---|---|
| 3,986,508 | 10/1976 | Barrington | 604/905 X |
| 4,596,571 | 6/1986 | Bellotti et al. | 604/411 |
| 4,981,469 | 1/1991 | Whitehouse et al. | 604/86 |
| 4,998,713 | 3/1991 | Vaillancourt | 604/283 |
| 5,057,093 | 10/1991 | Clegg et al. | 604/283 |
| 5,137,524 | 8/1992 | Lynn et al. | 604/283 |
| 5,139,483 | 8/1992 | Ryan | 604/86 |
| 5,158,554 | 10/1992 | Jepson et al. | 604/283 |

FOREIGN PATENT DOCUMENTS

| | | | |
|---|---|---|---|
| 8910770 | 11/1989 | World Int. Prop. O. | 604/192 |
| 9100116 | 1/1991 | World Int. Prop. O. | 604/192 |

Primary Examiner—C. Fred Rosenbaum
Assistant Examiner—Mark O. Polutta
Attorney, Agent, or Firm—Miller, Morriss & Pappas

[57] ABSTRACT

An improved, universally adaptable, medical intermediate connector having a large tubular opening at one end and a through passage running the length thereof, the body of the connector having a rectilinear cross section with plural planar sidewalls, one of the sidewalls having an extension with projecting fastening knobs and at least one of the sidewalls having a window therethrough, a resilient flexible and elongate strap selectively and adjustably attachable to the knobs and selectively extendable therefrom and returnable to the attachment knobs under tension. A cannula is secured to the body on the axis thereof and projects into the large tubular opening for communicating engagement with a septum inserted guidably into the tubular opening at one end and penetrable by the cannula. A luer socket is an axial extension of the body and communicates with the cannula via the passageway on the axis of the intermediate connector.

12 Claims, 3 Drawing Sheets

GUARDED NEEDLE AND RETAINING MEANS

The present invention is directed to an improved guarded needle intermediate connector and retaining means therefor universally adaptable to various styles and designs of intravenous sets, Y sites, T-Sites and plural Sites including manifolding and piggy back set ups and various forms of medical fluid handling and mixing best characterised in the handling of body fluids under sterile practice and including the addition and withdrawal of medicaments or body fluids to and from the course of the moving fluids.

BACKGROUND OF THE INVENTION

In medical science, the use of injection equipment has gone well beyond the relatively simple needle and syringe as usually thought of in injection of material into a patient or in the sampling of body fluids taken directly from the patient. Intravenous dosage and transfusion along with accurate and intermittent control of the flow of medication solutions and mixes of whole blood with medicaments and diluents has extended beyond the body, directly, and extends into reliance upon apparatus for achieving the selected mixing, dilution, treatment and manipulation of body fluids and even their return and reintroduction to the body of the patient. This has caused a proliferation of exotic equipment beyond the simplistic use of mere tubing to a source or from a source to a reservoir. In a sense the apparatus becomes an extension of the body of the patient to achieve central access to the body fluids for analysis modification and recirculation. This is especially true of blood. Many manufacturers of intravenous sets, in view of the desired sterile aspects of such apparatus, have developed tubing, tubing connectors, and injection apparatus at the connectors for sterile entry of the cannula or needle in gaining access to an intravenous fluid en route to or from the body of a patient and to which a variety of the connectors are useful at pre-located Y-Sites, T-Sites, Manifold Sites, with plural entries possible at the same point in a flow line to or from the patient.

Collaterally, the body fluids themselves contain contaminants which threaten the health and even life of doctors, technicians, and nurses using or encountering them at points where serious contact with the fluids may occur. The most difficult problem is that a very sharp needle is present at the injection site or point of use of the intermediate connector and shielding at that point is desireable to protect both the patient and medical personnel. A wide spectrum of shielding proposals have offered specific structures to match the particular manufactured (septum) entry and removal sites and without serious regard to interchangeability or adaptability for use with sites of different style and manufacture. The present structure seeks to achieve three principal objectives (a) relative universality (b) shielding of the needle and (c) retention means fixing the needle to other connector and site elements or apparatus against chance of accidental disconnection at the injection or access site.

Typical of prior art structures are the devices shown in U.S. Pat. No. 4,998,925 of Habib Al-Soufi et al shows a cylindrical sleeve-like extension shield jacketing the extending needle of a syringe and an extended sleeve to slidably cover selected injection caps, sites (septums) or luers as connected to tubing or apparatus pieces. The Al Sioufi device shows a form of sheathed connector with the needle mounted in the connector and the needle which, on one end of the needle axis, projects into the sleeve or sheath and on the other end is open into a luer lock. The tubular sheath portion includes a J-slot which bridges one of the extension legs of a Y-connector and allows the rotation of the shielded connector to secure the located shielded connector to a Y connector or fitting.

These various connectors and plural or manifold connector shapes create a problem since special fitting structures were required as the Y-Connectors vary from taper fits, keyed fits and special locks and caps at each nipple, or access point, to facilitate the selected sterile entry to the fluid and extraction of fluid, where desired.

The present invention demonstrates an ability to accommodate plural forms of connectors while providing a unique safety shield for the needle tip and universal tether means to secure the connection against chance loss while presenting rectilinear surfaces in prevention of loss of manual and tactile control by the personnel using the medical plural site devices either at the patient or remote from the patient being served. The intermediate connectors of the present invention are useable with a wide range of injection apparatus and tubular fluid conducting equipment as found in almost any particular laboratory or hospital for intravenous usage while maintaining acceptable structure accommodating sterile procedures and in shielded protection of patients and technical or professional personnel.

In addition, the presently described structure extends to technicians a visual control access over the scarf or needle through the wall of the protective shield while including a resilient and flexible strap means selectively in support relation to adjacent connected apparatus, patients, or dispensing attachments against chance dislodgement. This is achieved, partly by a shield wall extension from one of the planar walls, of the rectilinear sheath to serve as a guard for the needle and the extended wall enhances easy access for selected adjustable fastening means. The protruding planar shield provides additional tactile control.

Finally, the unit of the present invention provides a secured needle or cannula for establishing flow communication between at least two sites in an in-line relation and both selectively accommodating flow to and through the connection and for body fluids, chemicals, medicaments, food supplements, blood and blood fractions.

In general, the device of the present invention is an intermediate connector for use with conventional tubing fittings in which sterile techniques and apparatus are utilized in a plurality of medical and scientific flow relationships. Most notable are procedures in which blood or other body fluid is withdrawn from a patient through tubing that extends the flow from the body and then directs the flow for treatment or analysis and may return the fluid to the body in improved or treated condition to the patient. In the interval of removal, medicaments, additives and treatment or analysis is accomplished. Substantially the same apparatus may introduce transfused fluids or fluid fractions to the patient. This involves routines and protocol to assure protection from contamination of both patient and professional persons administering the procedures. In a typical use environment, the apparatus of many styles, manufacture sizes and shapes are found serving as fittings for the tubing. This is especially so where there must be an introduction or withdrawal of material to and from the flow line. The storage vessels for additives such as plasma sacks, whole blood containers and saline bottles and vacuum chamber tubes are usually fitted with penetrable self sealing entries but there always remains the problem of tapping the patient or the containers and controllably merging the flow of these fluids and then returning the enhanced or treated fluids to the body of the patient. This requires penetration of the seal at the entry to the patient or at entry to the container and from the container to the flow lines. Simplistically, the flow through the seals is by bolus injection via hypodermic syringes. The cannula of the syringe was driven through the rubber-like seal or septum site and additives introduced to the blood or the blood might be selectively withdrawn into the syringe.

Tubing-sets (for example IV-sets) flow the blood or fluids from the veins into the sterile tubing and the body fluid courses through the tubing to and through treatment stations such as found at injection sites and provided by Y-fittings capped with rubber penetrating seals at injection or withdrawal sites and which allow selected sterile penetration by cannula and the selected insertion of additives or selected withdrawal of fluids from the same ports as for analytical purposes. Valving and by-passes are utilized for flow control.

The emphasis on the design of prior art connectors is really an extension of the bolus utilization by syringe at junctures in the flow lines, at the points of receiving flow and at the points of juncturing two or more flowing fractions. In the present invention, the cannula plays a different role than as an intermittent injection fount. The thrust toward sterility involved covers or guards over the needles until the time of use. The many different styles of shielding of the user from the needle tips or scarfs are well known as in the U.S. Pat. No. of Bennett 4,419,098 (tubular closed ended tube cover for the needles or cannula); in the disclosures of U.S. Pat. No. 4,998,925 to Habib Al-Soufi shielding the needle by means of an adapter and by a connector achieving almost complete coverage of an extended cannula while aligning the cannula for seal or septum caps for cannula penetration into the flow line. The structures of Ogle II in U.S. Pat. Nos. 4,834,716 and Re 33,617 provide a cylindrical sheath with an arched cutout permitting needle access to a cap seal of a fitting without the extension of the cannula beyond the protected limits in at least two manners of use (1) where the cannula is carried by a syringe and the syringe penetrates the connector body and (2) where the cannula is embedded in the terminal insert in the body and insertion is provided with a cylindrical receiving entry for a septum access to a tubing flow line.

Vincent L. Vaillancourt U.S. Pat. No. 4,511,359 provides a two piece telescoping combination of a needle carrying cap and a male septum structure penetrable by the needle on its axis and lock tabs connecting the two upon axial connection.

George A. Lopez U.S. Pat. No. 4,752,292 provides two elongate connector elements one preventing access except by axial telescoping access in which a tubular septum ended conduit, upon axial insertion, impinges upon an axially extended cannula. A click lock external of a first tubular element and impinging on a second tubular element establishes when the septum seal is penetrated. Release is by releasing the click lock and separating the outer tubular element from the inner tubular element by axial straight line pull.

Jean M. Bonaldo in U.S. Pat. No. 4,950,260 utilizes a two part connector structure in which a cannula projects through and into a tubular housing and the housing includes an integrally hinged cover element. The second part of the connector is elongate and friction insertable into the housing with a septum cap on the tip of the inserted element arranged for receiving the scarf of the cannula in providing flow through the second element. The second element includes a latch closed upon folding down the hinged cover. Alignment is assured by registry with the flat bottoms and by the cover receiver recesses.

Charles B. Fields in U.S. Pat. No. 5,088,984 extends a cannula carrying member through a male luer threaded lock covered at its one end by a septum seal and at its other end equipped with a one way valve element with separate sleeve closing on a valve element, a six piece construction.

SUMMARY OF THE INVENTION

By contrast the present invention contemplates and asserts an intermediate connector structure with a resilient tether strap (separable in the preferred embodiment) for adjustable attachment of the connector to apparatus or to the wrist or arm of a patient or to a hospital bed, for example, to assure that the connection is firm and will not disengage. The strap may be on an integral hinge boded to the body extension material. In addition, the present invention provides a shroud of rectilinear cross section, for example, square or polygonal shielding for protecting users from accidental engagement with the needle scarf and provides visible access to the needle as an added assist in the coupling by the needle with the septum leg of a Y-fitting where the selected cap engages the scarf prior to guided entry into the rectilinear housing and the planar outer sides of the intermediate connector resulting shield-like in planar tubular sidewalls. The rectilinear cross section of the connector provides tactile consciousness to the user of the orientation of the connector cavity and is further aided by the tabular, rigid extension of the connector body which carries plural posts to selectively engage the perforations in the strap element. The cannula in the present device is fixed in the connector body and extends axially away from the shroud entry to the receiver socket or luer of the connector body. The receiver socket is in fact a luer lock connection providing the means for assurance of movement to flow lines in a sealed sterile (luer lock or taper) relationship opening into an integral coaxial luer connection. The passage provides an axial retention for a scarf tipped cannula that is sealed in the passage and extends into the shroud portion and substantially therethrough. At least one of the planar sides in the tubular shroud portion defines at least one window providing visual access by the technician to the cannula and the scarf portion thereof. The strap element, preferably stretchable and resilient, is removably secured to the intermediate connector body and is selectively extendable and terminally attachable to the extended planar wall portion of the intermediate connector body.

The device of the present invention is a universal guarded plastic flow connector structure possessing a rectilinear cross sectioned tubular and frontally open shroud portion in which one of the plural planar walls is integrally extended to form an outwardly extending shield and strap retaining platform and the shroud having a closing transverse wall at the opposite end of the end from the frontal opening. The transverse wall has a passage therethrough which is coaxial with the tubular shroud portion and defines a cylindrical extension on the axis of the intermediate connector and into a luer lock with tapered throat to achieve a tight connection to a wide range of tubing and fittings. The scarf of the cannula extends to or slightly beyond the open end of the planar tubular intermediate connector. Visual access to the cannula and its scarf is via a window through one of the planar walls of the connector. The extended of the planar walls projects outward and beyond the scarf and shields against accidental scarf contact by patients and technicians or medical personnel.

THE DESCRIPTION OF THE DRAWINGS

In the drawings there is presented the preferred embodiment of the presently described intermediate connector:

Figure 1:
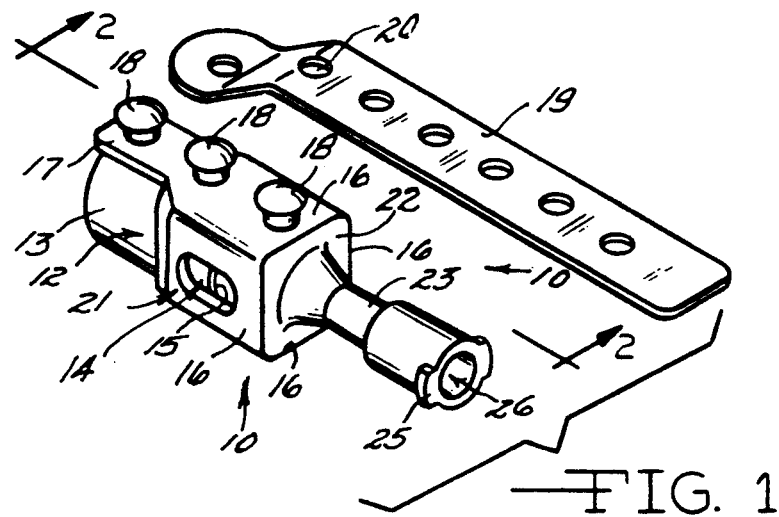
FIG. 1 is an exploded perspective view of an intermediate connector in accord with the present invention and with a separable restraining strap.
Figure 6:
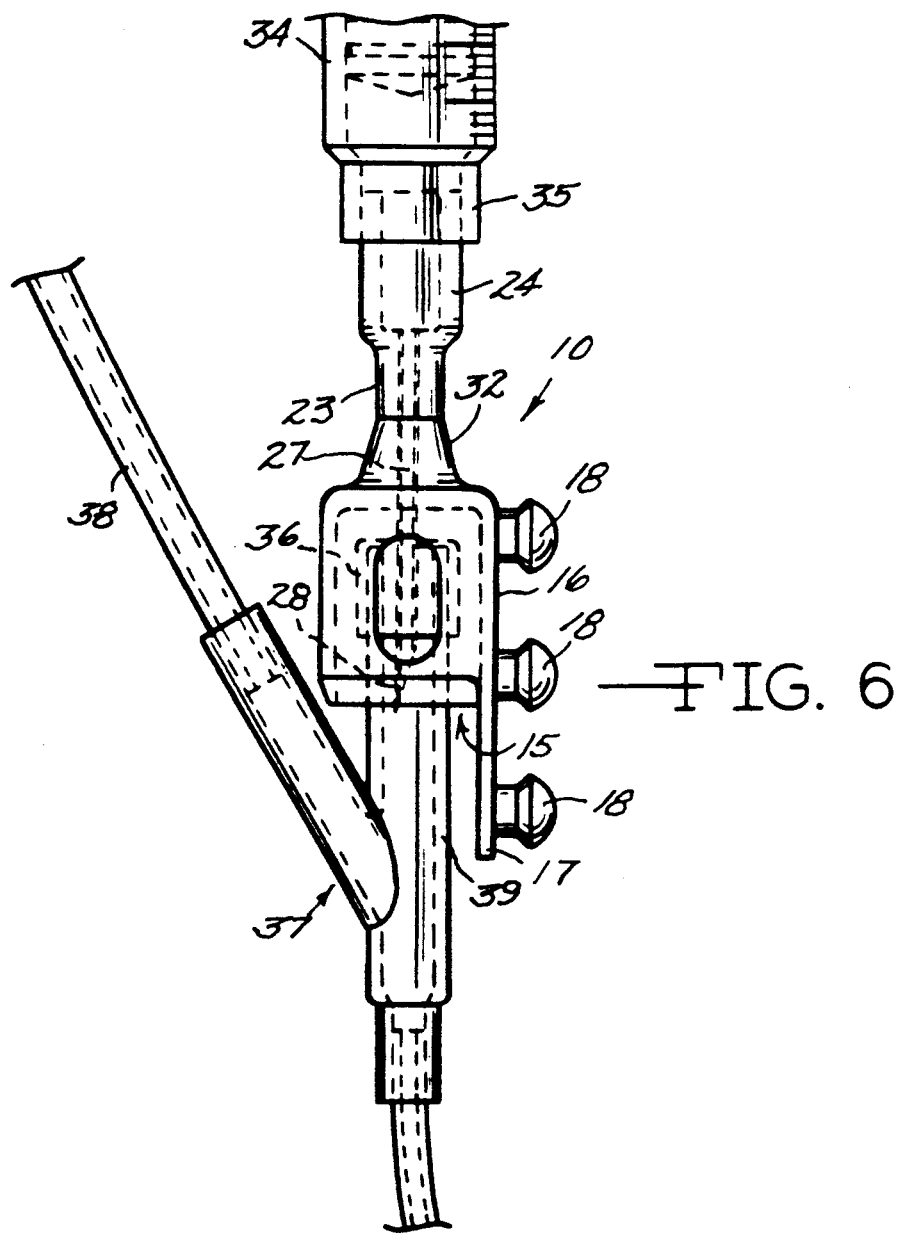

FIG. 6 is a side elevation view of the intermediate connector of FIG. 1 shown in a vertical position on a typical Y-connector leg and indicating the penetration by the cannula of the rubber septum or rubber septum cap and indicating a syringe attached to the luer of the intermediate connector whereby an intermittent bolus type injection may be provided via the intermittent syringe attachment at the luer. The visual access window is clearly indicated and the extension with strap fastening knobs shields against accidental user contact with the scarf of the cannula of the intermediate connection.

Figure 7:
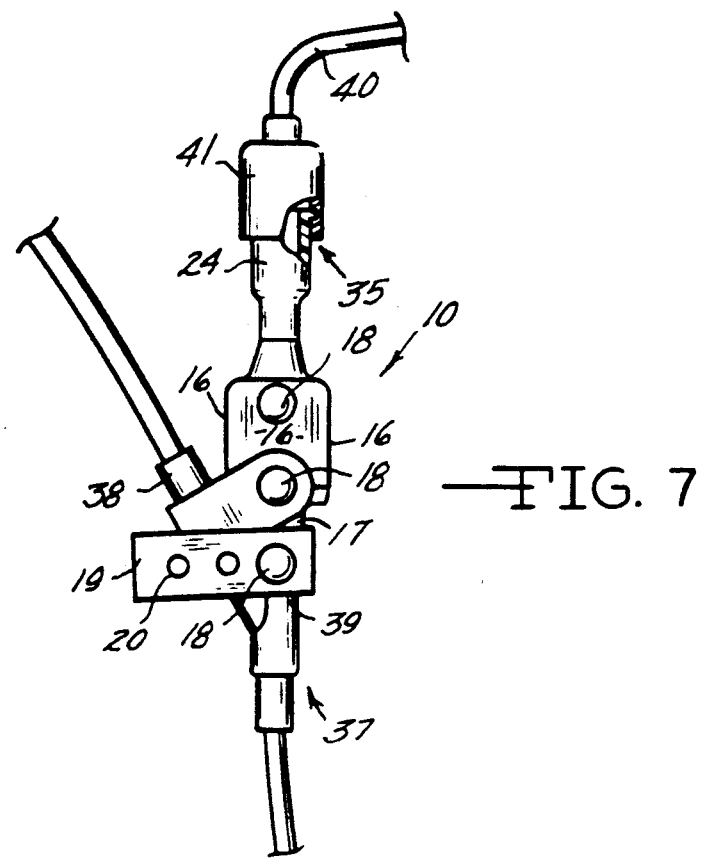

FIG. 7 is a side elevation view of the strap in retention of the intermediate connector to an access site in a multiport, Y-connector leg in which a tube-to-luer connection is achieved at the luer lock.

Figure 8:
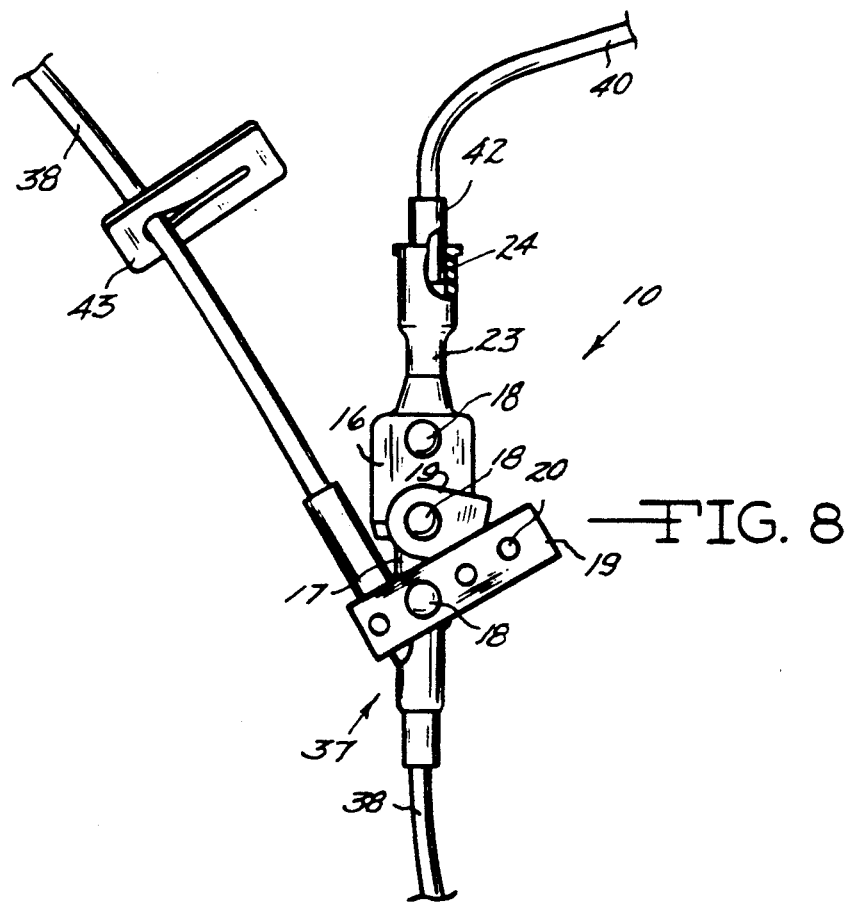

FIG. 8 is a side elevation view showing use of the strap seen in FIG. 7 acting to secure the Y-site structure to the intermediate connector against chance disengagement and further shielding chance access to the scarf and illustrating the use of the female luer taper to achieve a selected taper fit connection of tubing at the luer. The FIG. 8 also shows a typical tubing clamp as useable in such a set-up to selectively stop flow in the main line ahead of the Y-site connector.

DESCRIPTION OF THE PREFERRED EMBODIMENT

Referring to the drawings and with first specific reference to the FIG. 1, the intermediate medical tubular connector unit 10 is shown and comprises the rectilinear cross sectioned connector body 11 precision cast in preferably clear plastic (for example a copoethylene) integrally formed. The larger and tubular open shroud end 12 of the body 11 is covered by a removable tubular cup type needle cover 13 which frictionally telescopes into the larger guiding axial body cavity or opening 14 in a slip fit. The open end 15 of the cover 13 thus protectably covers the axially protruding needle or cannula as will be seen. One of the planar sides or sidewalls 16 of the body 10 includes a relatively rigid extension 17. The side of the body 16 and its projecting extension 17 includes upstanding plural fastening knobs 18. The elongate strap 19 with openings 20 therethrough at intervals is made of flexible and resilient material and, upon stretching the strap 19, the openings 20 selectively fit over and grip the knobs 18 and, in tension, permit secure attachment of the intermediate connector 10 to fittings or apparatus or patients, as desired. The windows 21, through the opposite sidewalls 16, permit visual observation of the interior of the body 10 and especially the disposition and orientation of the cannula, as will be seen.

Intermediate the length of the body 10 is a transverse wall 22 and the transverse wall 22 is integral with a tubular axial extension 23. The tubular extension 23 extends to include the coaxial luer socket 24 and the luer lock elements or projections 25. Tubular extension 23 defines an open passageway 26 axially extending into the body cavity 14 and through the wall 22. The strap 19 may be of silicone rubber, latex or other rubber-like material. The resin of the body 11 should be transparent, rigid upon curing and selected for casting or high precision injection molding. Both strap 19 and body 11 should be fabricated in a material that is stable in a sterilizing heat.

Figure 2:
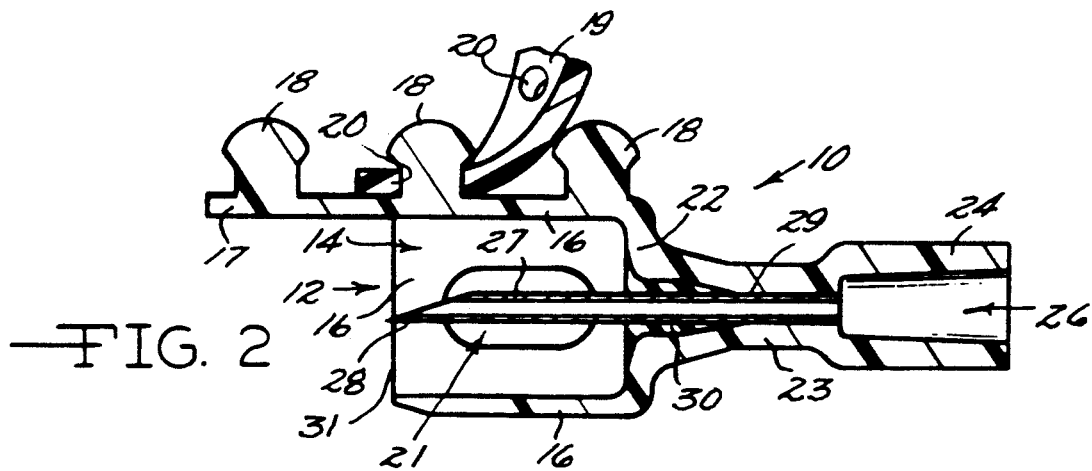
FIG. 2 is a full section side elevation view taken on the line 2—2 through the intermediate connector of FIG. 1.

The cross section in FIG. 2 through the axis of the intermediate connector unit 10, with the needle cover or cap 13 removed, best characterizes the positioning of the windows 21 and the planar extension or overhang 17 with the planar walls 16 which flank and define the axially oriented body cavity 14, open at the end adjacent the extension 17 so as to receive the needle cover or cap 13 which covers the cannula 27 and its scarf 28 (as in FIG. 1). In addition, the transverse wall 22 closing axially around the small axial opening 29 and through the cannula 22 provides an axial tubular extension 23 opening through the communication opening or passage 26 and through the cannula 27. The cannula 27 is axially secured in the extension or neck portion 23 as by heat sealing, adhesives, or cements 30 and is pressed into position through the tapered luer socket 24. The scarf 28 preferably extends a minor distance beyond the tapered lips 31 of the sides 16. In the FIG. 2 the tapered, chisel-like lips 31 of the planar walls at the open end 12 of the body 11 will be understood to assist in achieving a guided connection between the branches or legs in plural site fittings.

In the FIG. 2 the significance of visibility through the windows 21 is readily apparent. The wrap around capabilities of the strap 19 selectively anchored to a post 18 and wrapped securely as desired and pressed, via selected opening 20 in tensioned relation to another selected post 18 assures firmness of connection and location and avoids substantial risk to nurses and technicians faced with the job of securing a piggy back connection or anchoring a medical connector to apparatus and even to patients. By reference to the FIG. 2 in connection with FIGS. 3 and 4 the significance of the rectilinear cross section of the body 11 of the connector gains significance as it enhances tactile control via the "feel" of the connector in the hands of nurses and technicians at a point used in crisis or traumatic medical situations where safety, speed and precision are desired and where visibility and access is difficult. As contrasted with cylindrical shaped connector types, the planar extension 17 provides instant orientation and the fit of a system inserted in the open end 12 of the body 10 is easily and directly achieved.

While the square form of tubular cross section is shown, it will be appreciated that other polygonal cross sectional shapes with consequent planar walls are functional for tactile control where the planar surfaces provide tangential line contact with the cylindrical needle cover insert 13 and such variants are contemplated as within the spirit of the present invention.

Figure 3:
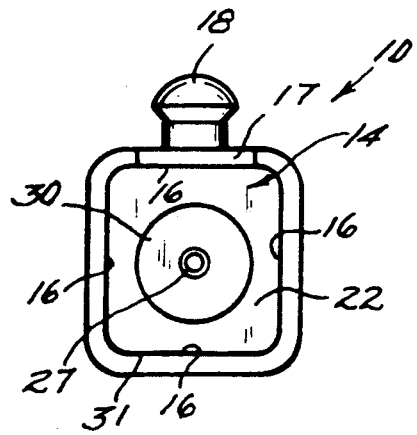
FIG. 3 is a front elevation view of the open end or shroud end of the structure of FIG. 1 and with the needle cover removed and scarf end of the cannula defining the small axial opening therethrough and revealing the planar character of the side walls forming the rectilinear cross sectional body.
Figure 4:
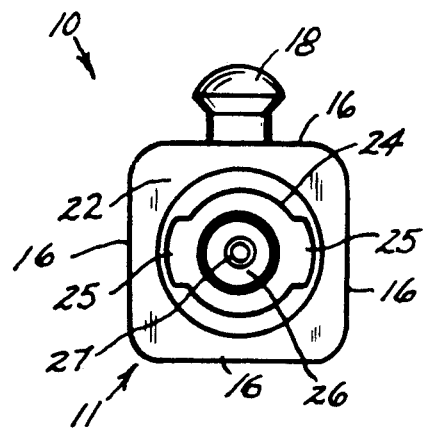
FIG. 4 is a rear end elevation view of the structure of FIG. 1 at the female luer socket end and looking through the axial passage of the cannula.

The FIGS. 3 and 4 dramatize the rectilinear character of the intermediate connector unit 10 with the straps 19 removed. At the open end of FIG. 3 the large body cavity 14 is well defined between the walls 16. The projecting extension portion 17, important to tactile orientation, is well understood in their attachment function. The transverse wall 22 and the axially oriented and secured cannula 27 projecting into the open cavity 14 and the securing of the cannula 27, peripherally, with axial access through the passage 26, is made very apparent. In addition, the chisel edge 31 of the sides 16 surrounding the entry to cavity 14 is made clear as a means to assist ultimate location in use.

The FIG. 4 provides another study in concentricity around the axis of the connector body 11 as best defined by a projection of the tubular or hollow cannula 27 running through the tapered luer socket 24 and into the open passage 26. The locking ears 25 of luer socket 24 provide access to optional types of connecting equipment.

Figure 5:
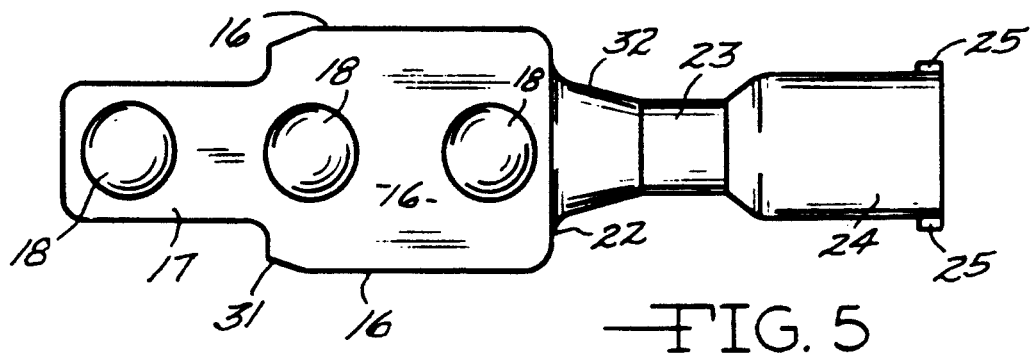
FIG. 5 is a top plan view of the intermediate connector of FIG. 1 with the cylindrical needle cover removed and best showing the extension of one of the planar side walls including the knob-like strap retainer posts.

The FIG. 5, shown without strap 19, provides an excellent representation of the simplicity of the intermediate connector 10 looking downward on the extension of one of sidewalls 16 to provide the shielding overhang forming the extension 17 with the knobs 18 which provide the fastening elements for the strap 19 as previously considered.

The symmetry of FIG. 5 in addition to the extension 17 and knobs 18 and the orientation by the luer socket 24 and locking ears 25 provide manual and tactile keys unappreciated in the prior art for attachment of the connector unit 10 to selected receiver apparatus.

By reference to FIG. 6, the intermediate connector unit 10 is presented in a typical operating setting in which an intermittent bolus syringe 34 with a luer lock fitting 35 is coupled to the luer lock socket 24 and the connector 10 is pressed down over an injection site of septum 36 in a set of tubing at a Y-connector 37 for a bolus injection of medication to main line 38 flow. Entry of the cannula 27 is observable through window 21 and the fit of the septum cap 36 on entry to the open tubular end 15 of the intermediate connector 10 guides the scarf 28 to proper penetrating contact for sterile entry and withdrawal from the septum 36.

The FIGS. 7 and 8 show typical applications of the intermediate connector unit 10 to the Y-site connector 37 through which the main flow line 38 passes. The site leg 39 with septum 36 (as in FIG. 6) is secured by the strap 19 under tension at the knobs 18 pressed through selected of the openings 20 in prevention of chance separation.

In FIG. 7 a secondary intravenous line 40 is shown coupled by the connector 10 to the Y-site connector 37 via a standard male luer connection 41 at the luer lock 35.

In FIG. 8 the coupling to the luer lock socket 24 is by a male tubing adaptor 42 inserted in the tapered receivers at the luer 35. The strap 19 is tensioned by stretching and selected fastening is by the utilization of the openings 20 placed over the knobs 18 (as in FIG. 2 and around the apparatus 37). The memory of the resilient material of the strap 19 assures a snug and shielding fitting. Such arrangements are generally known as "Piggy-Back" attachments entering to main flow lines 38 by way of the Y-connector 37.

In the FIG. 8 the main line tubing valve 43 provides a means in the main line for selected shut off of fluid flow useful in many set ups of both primary and secondary IV line flow sourcing from saline solutions, medication vials, nutrient and plasma bottles, bags and other sources including donors.

In addition, the uses extend to blood sampling by providing convenient access to blood without cannula scarf exposure to fingers and hands while providing good observatory and tactile orientation.

OPERATION

In operation, the devices of the present invention have demonstrated high utility and very good marks for safety for operators and patients alike. Retention of the structures in attachment to the Y-connectors, apparatus, and even patients, by means of the adjustable and extendable strap has significantly advanced the medical utility of the intermediate connectors. The design of the connector has resulted in injection molding simplicity and consequent manufacturing economies. The shape and tactile distinctions discussed have simplified use of the devices while avoiding accidents to patients and medical personnel. The sterile capabilities indicated have allowed an extended universality in the field-use adapting to various products of manufacturing sources of equipment.

Having thus described the invention in its preferred embodiment, those familiar in the medical and laboratory fields will readily extend the uses and versatility while improving and changing and modifying the structure and such changes, improvements and modifications within the skill of the art are intended to be included herein limited only by the scope of the hereinafter appended claims.

I claim:

1. A universal guarded plastic flow connector structure for use with medical flow apparatus comprising:
    a clear plastic intermediate connector body having a generally rectilinear cross sectioned tubular frontally open shroud portion, one of the planar sides of said shroud portion including a tabular elongate and longitudinal extension beyond said open shroud portion and said one side and said tabular extension having upstanding strap retaining means, said shroud portion having a closed transverse wall at the end opposite said tubular frontal opening and said transverse wall having an axial passage therethrough, defining a cylindrical tubular integral extension of said intermediate connector and said cylindrical tubular extension having an integral coaxial luer socket connection at the end thereof; a scarf tipped cannula axially supported and radially sealed in place within said axial passage and through said transverse wall and said scarf projecting into said open ended shroud portion, said scarf extending slightly beyond said open of said rectilinear shroud.

2. In the structure of claim 1 in which at least one other of said sides of said tubular shroud portion defines an open window for observation of said cannula.

3. In the structure of claim 2 wherein said luer socket connection is a female receiver type.

4. In the structure of claim 2 wherein said luer is a male type extension for socket connection.

5. In the structure of claim 2 wherein said luer sock connection is tapered.

6. In the structure of claim 1 and including a perforated strap, the perforations of said strap being resiliently extendable to fit over selected of said upstanding strap retaining means of said tubular extension for retaining said guarded flow connector in selected attachment to adjacent structure and fittings.

7. A guarded needle intermediate flow connector for use with medical tubular flow apparatus comprising:
an intermediate flow connector body defining a rectangular cross sectioned tubular frontally open shroud portion at one end and said shroud having at least one observation window assuring visibility into said shroud portion;
a wall barrier transversely positioned internally of and across said shroud portion of said body and defining an axial passage through said barrier;
a cannula supported in said passage through said wall barrier and extending axially-through said intermediate flow connector opposite said open shroud end and into which said axial passage penetrates;
a tubular luer socket integral with said body and in axial open flow communication through said intermediate flow connector means for attachment to a tubular fitting in tight flow relation; and
a flexible strap connected to one of the sides of said rectangular connector body and selectively extendable to selectively and releasably embrace ancillary structure.

8. An intermediate medical tubing connector comprising a generally tubular body having an open-ended tubular shroud portion and a extending tubular receiver portion in coaxial communication with said shroud portion; a cannula fixedly secured in said tubular receiver portion and having a scarf end extending into and slightly beyond said open end of said tubular shroud portion; a cup-like cylindrical cover frictionally insertable and removable in said open end of said shroud portion and selectively shielding said scarf of said cannula; a luer lock chamber in said receiver in flow communication with said shroud portion of said body; resilient strap means extending from said body of said connector; a longitudinal platform extension of said body from said open end of said shroud portion for adjustably supporting said strap; and upstanding posts selectively and for adjustably retaining said strap under tension in selected holding relation.

9. An intermediate medical flow connector device as set forth in claim 8 and further including openings through said shroud portion of said body providing windows whereby said cannula is readily observable.

10. In the medical flow connector of claim 8 wherein said luer chamber is tapered to receive tubing in a taper press fit.

11. In the medical flow connector of claim 8 wherein said luer is of a locking type.

12. In the medical flow connector of claim 11 wherein said luer includes means selectively lockable against chance removal from apparatus received thereby.

* * * * *